(12) United States Patent
Nakaya et al.

(10) Patent No.: US 10,438,785 B2
(45) Date of Patent: Oct. 8, 2019

(54) METHOD FOR QUANTITATIVE ANALYSIS OF HIGH-MOLECULAR COMPOUND AND DATA-PROCESSING DEVICE FOR THE QUANTITATIVE ANALYSIS

(71) Applicant: SHIMADZU CORPORATION, Kyoto-shi, Kyoto (JP)

(72) Inventors: Shuuichi Nakaya, Kyoto (JP); Shinji Funatsu, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 0 days.

(21) Appl. No.: 15/755,761

(22) PCT Filed: Aug. 31, 2015

(86) PCT No.: PCT/JP2015/074652
§ 371 (c)(1),
(2) Date: Jul. 26, 2018

(87) PCT Pub. No.: WO2017/037829
PCT Pub. Date: Mar. 9, 2017

(65) Prior Publication Data
US 2018/0337028 A1 Nov. 22, 2018

(51) Int. Cl.
*H01J 49/00* (2006.01)
*G01N 27/62* (2006.01)
(Continued)

(52) U.S. Cl.
CPC .......... *H01J 49/004* (2013.01); *G01N 27/62* (2013.01); *G01N 30/7233* (2013.01);
(Continued)

(58) Field of Classification Search
CPC .... H01J 49/00; H01J 49/0027; H01J 49/0031; H01J 49/0036; H01J 49/02
(Continued)

(56) References Cited

U.S. PATENT DOCUMENTS 8,653,448 B1   2/2014  Ueda et al.
2007/0048752 A1  3/2007  Yan et al.
(Continued)

FOREIGN PATENT DOCUMENTS

EP    1 994 413 A2    11/2008
JP    2009-526998 A    7/2009
(Continued)

OTHER PUBLICATIONS

Martin Pabst, et al., "Comparison of fluorescent labels for oligosaccharides and introduction of a new postlabeling purification method", Analytical Biochemistry, 2009, pp. 263-273, vol. 384.
(Continued)

*Primary Examiner* — Jason L McCormack
(74) *Attorney, Agent, or Firm* — Sughrue Mion, PLLC

(57) ABSTRACT

A method and apparatus for entering the structures of assumed sugar chains, assumed ionic numbers, m/z of a common product ion, etc. for calculating, by a precursor m/z calculator the m/z of precursor ions originating from each sugar chain. A method file creator prepares a method file including MRM transitions. A multivalent ion information file creator creates a file which associates a unique ID of each sugar-chain structure with m/z of precursor ions and m/z of a product ion. Then, a chromatogram creator creates a mass chromatogram for each MRM transition. A peak area totalizer adds up peak areas on mass chromatograms obtained for a plurality of MRM transitions corresponding to the same sugar chain. Based on the calculated total values, a quantitative value calculator calculates an abundance ratio of each sugar chain as a quantitative value. A quantitative output information creator displays the quantitative values on a display unit.

9 Claims, 6 Drawing Sheets

(51) Int. Cl.
 *G01N 30/72* (2006.01)
 *G01N 30/88* (2006.01)

(52) U.S. Cl.
 CPC .......... *G01N 30/88* (2013.01); *H01J 49/0036* (2013.01); *G01N 2030/8831* (2013.01)

(58) Field of Classification Search
 USPC .................................................. 250/281, 282
 See application file for complete search history.

(56) References Cited

U.S. PATENT DOCUMENTS

| | | | |
|---|---|---|---|
| 2012/0164741 A1 | 6/2012 | Chen et al. | |
| 2013/0040857 A1* | 2/2013 | Anderson | G01N 33/6848 506/12 |
| 2014/0350020 A1* | 11/2014 | Follmann | A61K 45/06 514/243 |

FOREIGN PATENT DOCUMENTS

| | | |
|---|---|---|
| JP | 2014-066704 A | 4/2014 |
| JP | 2014-66704 A | 4/2014 |
| JP | 2014-130134 A | 7/2014 |
| KR | 10-2014-0032871 A | 3/2014 |
| WO | 2007/100506 A2 | 9/2007 |

OTHER PUBLICATIONS

Chengjian Wang, et al., "Separation of one-pot procedure released O-glycans as 1-phenyl-3-methyl-5-pyrazolone derivatives by hydrophilic interaction and reversed-phase liquid chromatography followed by identification using electrospray mass spectrometry and tandem mass spectrometry", Journal of Chromatography A, 2013, pp. 107-117, vol. 1274.

Yoshinao Wada, et al., Hydrophilic Affinity Isolation and MALDI Multiple-Stage Tandem Mass Spectrometry of Glycopeptides for Glycoproteomics:, Analytical Chemistry, 2004, pp. 6560-6565, vol. 76.

Chengjian Wang, et al., "One-pot nonreductive O-glycan release and labeling with 1-phenyl-3-methyl-5-pyrazolone followed by ESI-MS analysis", Proteomics, 2011, 4229-4242, vol. 11.

International Search Report for PCT/2015/074652 dated Nov. 24, 2015 (PCT/ISA/210).

International Search Report for PCT/JP2015/074652 dated Nov. 24, 2015 (PCT/ISA/210).

Communication dated Jun. 26, 2019, from the European Patent Office in application No. 15902952.9.

* cited by examiner

METHOD FOR QUANTITATIVE ANALYSIS OF HIGH-MOLECULAR COMPOUND AND DATA-PROCESSING DEVICE FOR THE QUANTITATIVE ANALYSIS

TECHNICAL FIELD

The present invention relates to a method for a quantitative analysis for determining the quantity of a high-molecular compound, such as a sugar chain or glycopeptide in a sample, as well as a data-processing device for the quantitative analysis. More specifically, it relates to a method for determining the quantity of a high-molecular compound in a sample using a mass spectrometer capable of an MS/MS analysis, as well as a data-processing device for the same method.

BACKGROUND ART

A multiple reaction monitoring (MRM) measurement using a liquid chromatograph mass spectrometer (LC-MS) which includes the combination of a liquid chromatograph and a tandem quadrupole mass spectrometer has been frequently used for quantitative analyses of low-molecular compounds, such as drugs or agricultural chemicals. In an MRM measurement, influences of foreign components can be removed by two-stage mass separators (quadrupole mass filters). Therefore, a quantitative analysis of a target component can be performed with high accuracy even in the case where there is a foreign component having a retention time close to that of the target component and the two components cannot be sufficiently separated from each other in the liquid chromatograph. Furthermore, in an MRM measurement using an LC-MS, it is normally possible to set a plurality of combinations of precursor ion and product ion (which are generally called "MRM transitions") within one measurement time range, allowing for a quantitative determination of several tens of kinds of components or even a hundred and several tens of kinds of components by a single measurement. Such an analytical technique is called the "simultaneous multicomponent analysis". In recent years, this technique has been widely used for the testing of residual agricultural chemicals, testing of contaminants in environmental water, and other purposes.

On the other hand, for quantitative analyses of high-molecular compounds, such as sugar chains or glycopeptides, liquid chromatographs employing an ultraviolet absorption detector or fluorescent detector as the detector are still frequently used (for example, see Non Patent Literature 1 or 2). One of the reasons is as follows: In LC-MS, ion sources which employ electrospray ionization (ESI) or similar methods are commonly used. If a high-molecular compound, such as a sugar chain or glycopeptide, is ionized by such an ion source, a plurality of kinds of multivalent ions whose valency is not one are easily generated. Accordingly, unlike the case of the low-molecular compounds, the simple combination of one precursor ion and one product ion cannot always be obtained for each component. There is also another problem. i.e. as is commonly known, sugar chains have non-uniformity in structure, which causes the detected ionic valencies to considerably vary depending on the sample. Due to these problems, unlike the quantitative analysis of a low-molecular compound, it is difficult to perform a simultaneous multicomponent analysis using an LC-MS in the case of a quantitative analysis of a high-molecular compound, such as a sugar chain or glycopeptide. Consequently, it is necessary to perform a quantitative analysis for each individual compound using a liquid chromatograph which employs an ultraviolet absorption detector or fluorescent detector as the detector. Such an analysis is low in throughput. Thus, a reduction in the time and labor necessary for the analysis has been a major challenge.

CITATION LIST

Patent Literature

Patent Literature 1: JP 2014-66704 A

Non Patent Literature

Non Patent Literature 1: Martin Pabst and six other authors, "Comparison of fluorescent labels for oligosaccharides and introduction of a new postlabeling purification method", Analytical Biochemistry, Vol. 384, 2009. pp. 263-273

Non Patent Literature 2: Chengjian Wang and three other authors, "Separation of one-pot procedure released O-glycans as 1-phenyl-3-methyl-5-pyrazolone derivatives by hydrophilic interaction and reversed-phase liquid chromatography followed by identification using electrospray mass spectrometry and tandem mass spectrometry", Journal of Chromatography A, Vol. 1274, 2013, pp. 107-117

Non Patent Literature 3: Y. Wada and two other authors, "Hydrophilic affinity isolation and MALDI multiple-stage tandem mass spectrometry of glycopeptides for glycoproteomics", Analytical Chemistry. Vol. 76, 2004, pp. 6560-6565

Non Patent Literature 4: Chengjian Wang and four other authors, "One-pot nonreductive O-glycan release and labeling with 1-phenyl-3-methyl-5-pyrazolone followed by ESI-MS analysis", Proteomics, Vol. 11, 2011, pp. 4229-4242

SUMMARY OF INVENTION

Technical Problem

The present invention has been developed to solve the previously described problem. Its objective is to provide a method for a quantitative analysis of a high-molecular compound as well as a data-processing device for carrying out the same method which make it possible to perform a simultaneous multicomponent analysis for sugar chains, glycopeptides or similar high-molecular compounds using an MRM measurement in a device which includes, for example, the combination of a liquid chromatograph and a quadrupole mass spectrometer or other types of mass spectrometers capable of an MS/MS analysis, to enhance the throughput of a quantitative analysis of those high-molecular compounds.

Solution to Problem

The method for a quantitative analysis of a high-molecular compound according to the present invention developed for solving the previously described problem is a method for a quantitative analysis for determining the quantity of a high-molecular compound in a sample using a mass spectrometer capable of an MS/MS analysis, the method including:

a) a peak information acquisition step, in which a total value of the areas of peaks appearing on a plurality of mass chromatograms respectively acquired by a plurality of MRM measurements is calculated for a high-molecular compound which is an analysis target or is assumed to be an analysis target, the plurality of MRM measurements performed for a plurality of precursor ions which originate from the high-molecular compound yet differ from each other in ionic valency and one product ion which is common to the precursor ions; and b) a quantitative determination step, in which a quantity calculation of the high-molecular compound which is the analysis target or is assumed to be the analysis target is performed using the total value obtained in the peak information acquisition step.

A data-processing device for a quantitative analysis of a high-molecular compound according to the present invention developed for solving the previously described problem is a device for carrying out the previously described method for a quantitative analysis. In a data-processing device for determining the quantity of a high-molecular compound in a sample based on data acquired by using a mass spectrometer capable of an MS/MS analysis, the data-processing device according to the present invention includes:

a) a peak information acquirer for calculating a total value of the areas of peaks appearing on a plurality of mass chromatograms respectively acquired by a plurality of MRM measurements for a high-molecular compound which is an analysis target or is assumed to be an analysis target, the plurality of MRM measurements performed for a plurality of precursor ions which originate from the high-molecular compound yet differ from each other in ionic valency and one precursor ion which is common to the precursor ions; and b) a quantitative determination processor for performing a quantity calculation of the high-molecular compound which is the analysis target or is assumed to be the analysis target, using the total value obtained by the peak information acquirer.

In the method and data-processing device for a quantitative analysis of a high-molecular compound according to the present invention, the mass spectrometer for acquiring data to be processed may typically be: a tandem quadrupole mass spectrometer in which two quadrupole mass filters are respectively located on the front and rear sides of a collision cell; a Q-TOF mass spectrometer in which a time-of-flight mass spectrometer is used in place of the rear-side quadrupole mass filter in the tandem quadrupole mass spectrometer; or a TOF/TOF mass spectrometer in which two time-of-flight mass separators are connected in series, with a collision cell and an ion gate in between. The mass spectrometer used in the present invention may preferably be a mass spectrometer which employs an ion source that tends to produce multivalent ions. An example of such an ion source is one which employs an atmospheric pressure ionization method, such as the ESI method mentioned earlier.

In the method and data-processing device for a quantitative analysis of a high-molecular compound according to the present invention, a typical example of the high-molecular compound to be analyzed is a sugar chain or glycopeptide, because sugar chains and glycopeptides generate a known kind of common product ion through the fragmentation of their precursor ions despite the structural difference of the sugar chains or glycopeptides concerned.

For example, for N-linked glycopeptides or labeled N-linked sugar chains labelled with 2-aminopyridine or similar substances, a product ion having a mass-to-charge ratio of m/z 138, which originates from the core structure (3Hex-2HexNac) of N-linked sugar chains, can be used as the common product ion (see Patent Literature 1). For PMP-labelled O-linked sugar chains labelled with 1-phenyl-3-Methyl-5-pyrazolone (PMP), a production ion having a mass-to-charge ratio of m/z 175, which originates from the complete molecule of PMP which is preferentially desorbed by fragmentation, can be used as the common product ion.

In the case where a plurality of multivalent ions having different ionic valencies are generated from one high-molecular compound, it is certainly possible to determine an MRM transition for every ionic valency within a predetermined range and perform the MRM measurement for all MRM transitions. However, if the number of MRM transitions per one compound is large, the period of time for the MRM measurement under one MRM transition will be short, or the time interval of the repetition of the MRM measurement under the same MRM transition will be long. The former situation leads to a deterioration in analysis sensitivity, while the latter situation leads to a deterioration in the quantitative accuracy. To address this problem, the data-processing device according to the present invention may preferably be configured to allow an analysis operator to enter and set information on the compound, information on the ionic valency, and information on the product ion. For some kinds of high-molecular compounds, such as sugar chains or glycopeptides, analysis operators can refer to empirical information and estimate, to a certain degree, the range of ionic valencies of the ions which will be generated, for example, in an ionization process by an ESI method. By entering and setting the information based on such estimations, they can avoid unnecessary measurements from which no useful data will be obtained.

In the method for a quantitative analysis of a high-molecular compound according to the present invention, a total of the areas of the peaks which originate from one target compound and appear on mass chromatograms respectively obtained by a plurality of MRM measurements performed for the target compound is calculated in the peak information acquisition step. In this calculation, a peak area determined from a mass chromatogram obtained by one MRM measurement reflects the amount of ion having one specific ionic valency originating from the target compound. Accordingly, by totaling the plurality of peak areas which respectively reflect the amounts of ions which originate from the target compound and yet have different ionic valencies, a total value which reflects the amount of ions independent of the ionic valency is calculated, and this total value is used for the quantitative determination of the target compound. For example, if the sample is a mixture of sugar chains or glycopeptides, the abundance ratio of each sugar chain or glycopeptide in the sample can be calculated by performing measurements which almost exhaustively cover the sugar chains or glycopeptides in the sample, and then calculating the total value of the peak areas for each sugar chain or glycopeptide based on the measured result.

In order to perform such a calculation and output the calculated result, the data-processing device for a quantitative analysis of a high-molecular compound according to the present may be configured as follows:

the sample is a mixture of sugar chains or glycopeptides;

the peak information acquirer obtains the total values respectively for a plurality of sugar chains or glycopeptides contained in the sample;

the quantitative determination processor determines an abundance ratio of any specific sugar chain or glycopeptide, based on the total value obtained for the specific sugar chain or glycopeptide by the peak information acquirer and the sum of the total values obtained for the plurality of sugar chains or glycopeptides contained in the sample; and the data-processing device further includes a quantitative determination result presenter for presenting the abundance ratio of the specific sugar chain or glycopeptide obtained by the quantitative determination processor, in a graphical or tabular form on a screen of a display section.

It is not always necessary to use an LC-MS in which a sample containing a compound separated into components by a liquid chromatograph is introduced into a mass spectrometer in the previously described manner, in order to obtain the data to be processed in the method and data-processing device for a quantitative analysis of a high-molecular compound according to the present invention. However, it is preferable to use an LC-MS to obtain data in the case of a simultaneous multicomponent analysis, and particularly, in the case of determining the quantities of sugar chains or similar compounds which are identical in mass and have various structures.

Advantageous Effects of the Invention

With the method for a quantitative analysis of a high-molecular compound and the data-processing device for the same quantitative analysis according to the present invention, it is possible to use an MRM measurement in a mass spectrometer capable of an MS/MS analysis to efficiently and accurately determine the quantity of a sugar chain, glycopeptide or similar high-molecular compound from which a plurality of kinds of multivalent ions are easily generated in an ionization process. In particular, an LC-MS can be used to perform a simultaneous multicomponent analysis for a mixture of sugar chains or glycopeptides, or a similar sample. This improves the throughput of a quantitative analysis of those high-molecular compounds, so that a reduction of the time and labor necessary for the analysis can be achieved.

DESCRIPTION OF EMBODIMENTS

One embodiment of the method for a quantitative analysis of a high-molecular compound and a data-processing device for carrying out the same method according to the present invention is hereinafter described with reference to the attached drawings. The following description deals with the case of determining the quantities of sugar chains or glycopeptides in a sample which is a mixture of sugar chains or glycopeptides.

Figure 1:
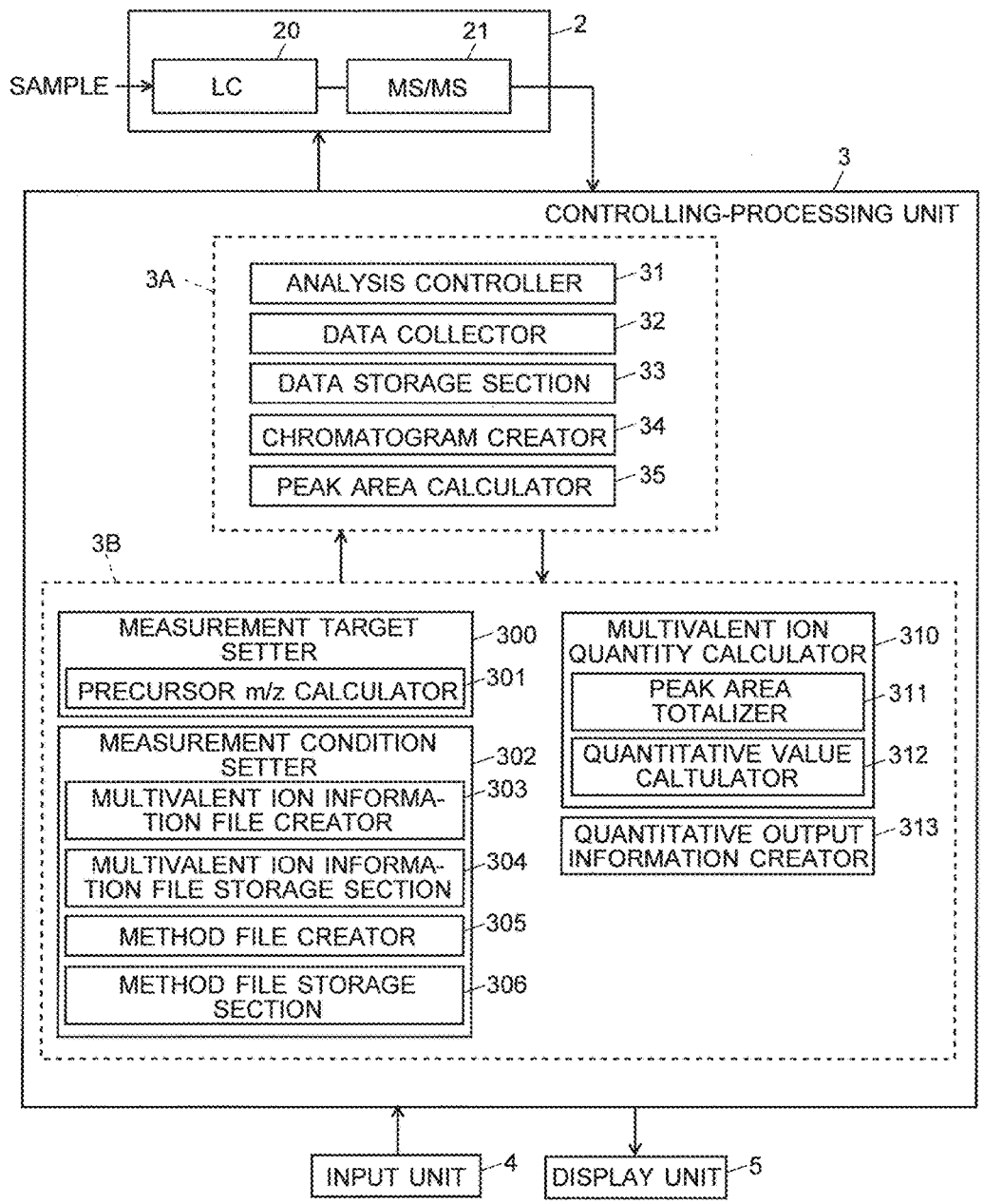
FIG. 1 is a schematic configuration diagram of a quantitative analyzer as one embodiment of the present invention.

FIG. 1 is a schematic configuration diagram of a quantitative analyzer in the present embodiment which includes a data-processing device according to the present invention.

The present quantitative analyzer includes: a measurement unit 2 including a liquid chromatograph (LC) 20 and a tandem quadrupole mass spectrometer (MS/MS) 21; a controlling-processing unit 3 for controlling operations of the measurement unit 2 and for processing data obtained with the measurement unit 2; as well as an input unit 4 and a display unit 5 which are user interfaces.

Though not shown, the liquid chromatograph 20 includes: a liquid-supply pump for supplying a mobile phase; an injector for injecting a sample into the mobile phase; a column for temporally separating components in a sample; and other elements. The tandem quadrupole mass spectrometer 21 includes an ESI ion source for ionizing components in a liquid sample eluted from the column, as well as a front quadrupole mass filter, collision cell, rear quadrupole mass filter, detector and other elements. The tandem quadrupole mass spectrometer 21 may be replaced by a different form of mass spectrometer capable of an MS/MS analysis, such as a Q-TOF mass spectrometer.

Normally, the controlling-processing unit 3 is actually a personal computer or more sophisticated workstation (it should be noted that they are not always a single computer; they may be a plurality of computers connected to each other), on which one or more dedicated controlling-processing software programs are installed. The functional blocks included in the controlling-processing unit 3 are embodied by those programs running on the computer.

Specifically, the controlling-processing unit 3 has the following functional blocks embodied by an existing controlling-processing software program (indicated by numeral 3A in FIG. 1): an analysis controller 31, data collector 32, data storage section 33, chromatogram creator 34, and peak area calculator 35. The controlling-processing unit 3 also has the following functional blocks (indicated by numeral 3B in FIG. 1) embodied by a newly prepared controlling-processing software program to execute characteristic data-processing operations (which will be described later): a measurement target setter 300, which includes a precursor m/z calculator 301; a measurement condition setter 302, which includes a multivalent ion information file creator 303, multivalent ion information file storage section 304, method file creator 305, and method file storage section 306; a multivalent ion quantity calculator 310, which includes a peak area totalizer 311 and quantitative value calculator 312; and a quantitative output information creator 313. Naturally, the functional blocks indicated by numerals 3A and 3B in FIG. 1 may be embodied by a single controlling-processing software program.

The sample to be subjected to the measurement is, for example, a mixture of N-linked glycopeptides, mixture of labelled N-linked sugar chains, or mixture of PMP-labelled O-linked sugar chains. Any of these compounds is prepared through a predetermined pretreatment. For example, N-linked glycopeptides are prepared by digesting a glycoprotein, such as an antibody, with an appropriate enzyme, such as trypsin, and then treating them by a method based on the method described in Non Patent Literature 3. Labelled N-linked sugar chains are prepared, for example, by treating sugar chains with glycanase, such as PNGase, and subsequently labelling them with 2-aminopyridine. PMP-labelled O-linked sugar chains are prepared, for example, by nonreductive alkaline i-elimination and PMP-labelling, based on the method described in Non Patent Literature 4.

In advance of the measurement of the previously described type of sample with the measurement unit 2, an analysis operator enters measurement conditions from an input unit 4, which includes a keyboard and other devices. The analysis operator initially enters and sets the structures of various sugar chains which are assumed to be contained in the sample, ionic valencies of the ions (precursor ions) which are assumed to be generated from those sugar chains, and mass-to-charge ratio of a product ion which will commonly appear regardless of the structure of the sugar chain.

Specifically, the analysis operator performs a predetermined operation using the input unit 4. Then, the measurement target setter 300 displays a list of structures of various sugar chains on the screen of the display unit 5. From this list, the analysis operator selects a plurality of sugar-chain structures which are assumed to be contained in the sample and enters a plurality of ionic valencies for each selected structure. The mass of each sugar-chain structure is previously known. Therefore, for each sugar-chain structure, the precursor m/z calculator 301 calculates the mass-to-charge ratios of the ions originating from that sugar-chain structure as the precursor-ion mass-to-charge ratios, based on the mass of the sugar chain concerned and the entered ionic valencies.

The measurement target setter 300 also displays a list of candidates of the mass-to-charge ratios of the product ions on the screen of the display unit 5. The analysis operator selects an appropriate mass-to-charge ratio from the list according to the kind of sample and other relevant factors. The mass-to-charge ratio of the product ion normally depends on the trunk structure of the sugar chain. If the components in the sample are N-linked glycopeptides or labelled N-linked sugar chains, m/z 138 can be selected as the mass-to-charge ratio of the product ion, as disclosed in Patent Literature 1. This is an ion which originates from the core structure (3Hex-2HexNac) of the N-linked sugar chains. If the components in the sample are PMP-labelled O-linked sugar chains, m/z 175 can be selected as the mass-to-charge ratio of the product ion, as described in the Japanese Patent Application No. 2015-83846, which is a prior application by the present applicant. This is an ion which originates from the complete molecule of PMP which is preferentially desorbed by fragmentation.

Figure 3:
FIG. 3 is a table showing one example the combinations of precursor ions which are multivalent ions and a common product ion in the quantitative analyzer according to the present embodiment.

As a result of the previously described processing, the mass-to-charge ratios of a number of precursor ions and that of a product ion are determined. In other words, a number of MRM transitions each of which consists of the mass-to-charge ratio of one precursor ion combined with the mass-to-charge ratio of one product ion are determined. FIG. 3 is a table showing one example of the MRM transitions, i.e. the combinations of precursor ions, which are multivalent ions, and a common product ion. For example, the first row in FIG. 3 shows the combination of a trivalent precursor ion having a mass-to-charge ratio of m/z 986.7225 and a product ion having a mass-to-charge ratio of m/z 138.

Furthermore, the analysis operator using the input unit 4 enters measurement conditions, such as a measurement time range and the MRM transition of an MRM measurement to be performed within that measurement time range, on the measurement condition setting window displayed by the measurement condition setter 302 on the screen of the display unit 5. Normally, the measurement time range is appropriately determined based on the known retention time of an assumed sugar chain.

After the measurement conditions have been set in the previously described manner, the method file creator 305 creates a method file for controlling the relevant sections of the measurement unit to repeatedly perform an MRM measurement for one or a plurality of MRM transitions within a period of time from the specified beginning time to the ending time, with the point of sample injection defined as the time of zero. If a single MRM transition is set for the MRM measurement within a certain measurement time range, the MRM measurement for that MRM transition will be repeatedly performed. If a plurality of MRM transitions are set for the MRM measurement within a certain measurement time range, a cyclic process in which the MRM measurements for the plurality of MRM transitions are each carried out one time will be repeatedly performed. The created method file is stored in the method file storage section 306.

The multivalent ion information file creator 303 creates a multivalent ion information file which associates a unique identifier (ID), which is assigned to each sugar-chain structure, with the mass-to-charge ratios of a plurality of precursor ions which originate from the sugar chain concerned and have different ionic valencies as well as the mass-to-charge ratio of the common product ion. The created file is stored in the multivalent ion information file storage section 304.

Figure 2:
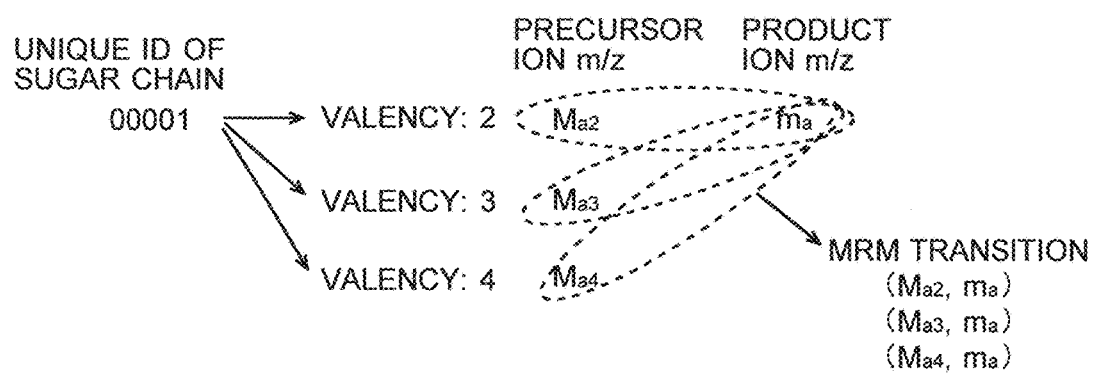
FIG. 2 is an illustration showing one example of the association of a compound to be analyzed with precursor ions and a product ion in the quantitative analyzer according to the present embodiment.

FIG. 2 is an illustration showing one example of the association. In this example, a unique identifier by which the sugar-chain structure can be identified is connected with the mass-to-charge ratios of three precursor ions having ionic valencies of two, three and four as well as the mass-to-charge ratio of one product ion common to those precursor ions. In the present case, there are three different MRM transitions for the sugar chain concerned. The reason for preparing a file for such an association is because the method file mentioned earlier merely relates MRM transitions to a measurement time range and does not relate MRM transitions to compounds (in the present case, the structures of sugar chains or glycopeptides).

For example, when a command to initiate an analysis has been issued by the analysis operator, the analysis controller 31 performs an LC/MS analysis for the sample by controlling the measurement unit 2 according to the measurement conditions in the method file saved in the method file storage section 306. That is to say, for various compounds eluted from the column of the liquid chromatograph 20, MRM measurements for various MRM transitions are sequentially performed in the tandem quadrupole mass spectrometer 21. The data collector 32 collects data obtained from the tandem quadrupole mass spectrometer 21 and save them as a single data file in the data storage section 33.

After the completion of the measurement, the analysis operator issues a command to execute the quantitative determination process. Then, the chromatogram creator 34 reads the specified data file from the data storage section 33 and creates, for each MRM transition, a mass chromatogram showing the relationship between time and signal intensity based on the data obtained by the MRM measurement.

Figure 4:
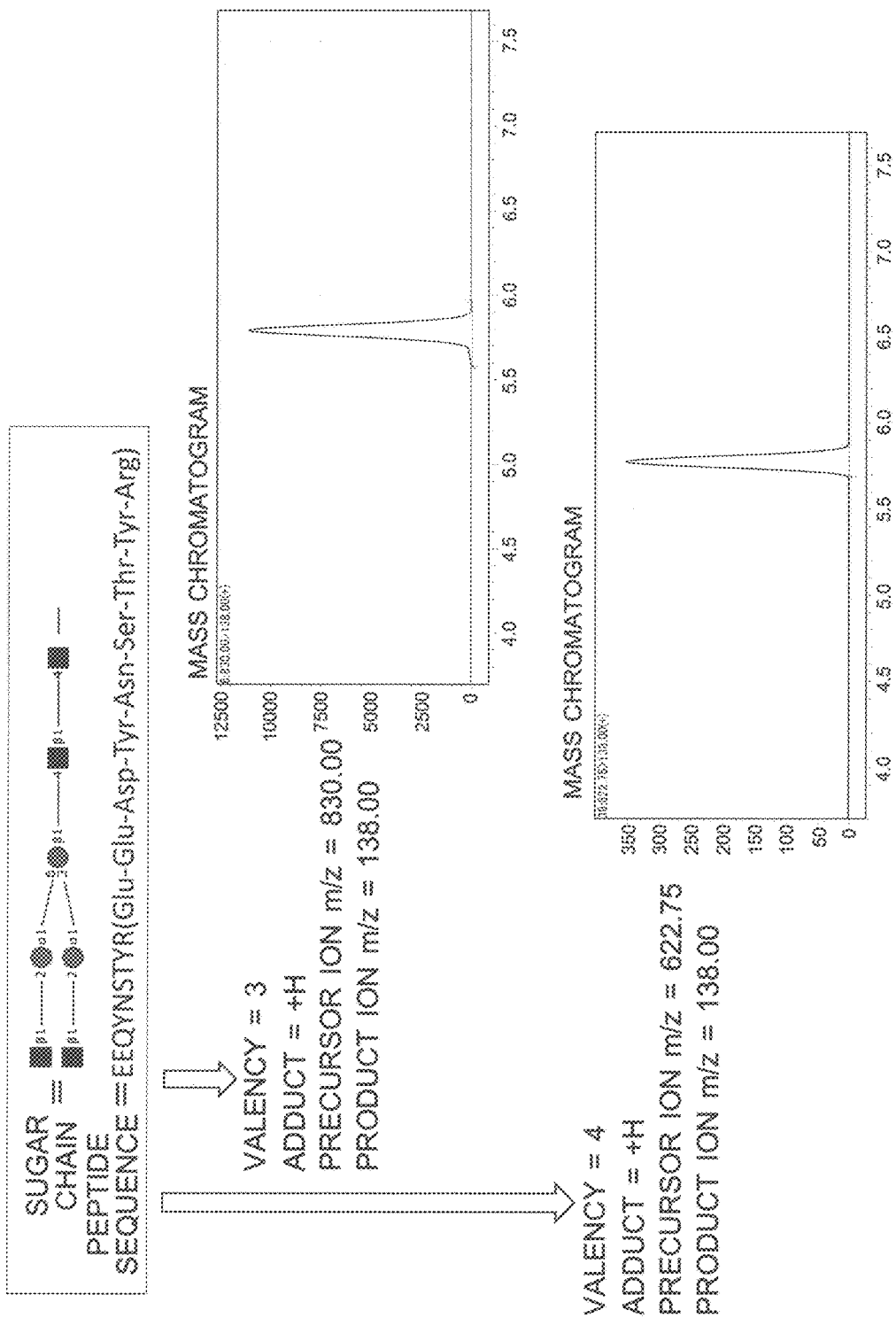
FIG. 4 is a diagram showing examples of mass chromatograms obtained in the quantitative analyzer according to the present embodiment for a plurality of MRM transitions originating from the same sugar chain.
Figure 5:
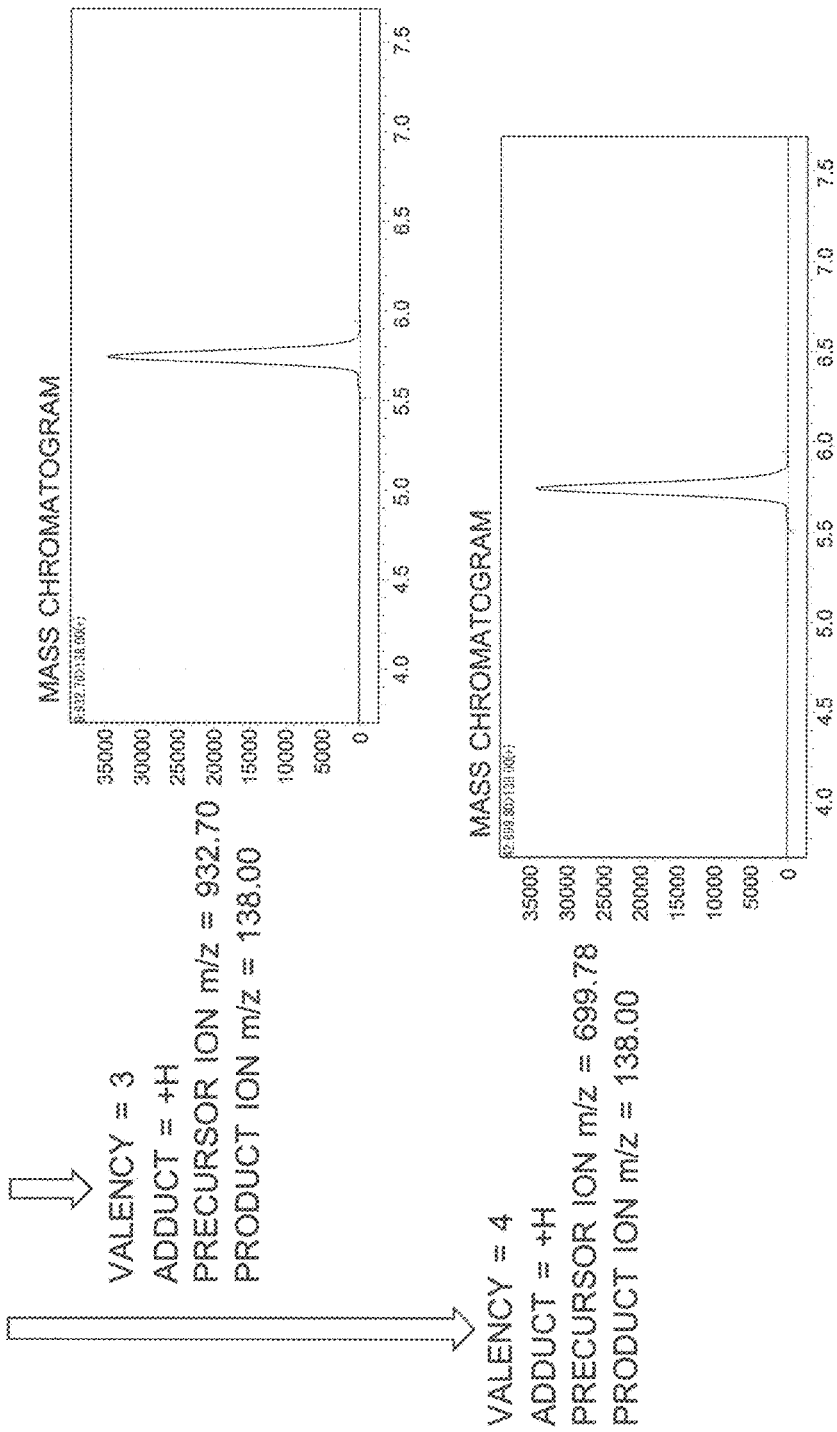
FIG. 5 is a diagram showing other examples of mass chromatograms obtained in the quantitative analyzer according to the present embodiment for a plurality of MRM transitions originating from the same sugar chain.

FIGS. 4 and 5 show examples of the mass chromatograms created in the previously described manner. In those examples, an isolated peak is present on each mass chromatogram. It is evident that such a peak originates from the (assumed) target sugar chain or glycopeptide. However, in some cases, a plurality of peaks which originate from a plurality of sugar chains may appear on one mass chromatogram. For example, such a situation occurs when there are a plurality of sugar chains or glycopeptides which have the same composition and merely differ from each other in structure. In such a case, it is necessary to identify the target sugar chain or glycopeptide and separate it from the other sugar chains or glycopeptides. To this end, the analysis operator operates the device to display each mass chromatogram on the screen of the display unit 5 and checks the peak(s) on the screen. If necessary, the analysis operator specifies an allowable range of the detection time for detecting the peak of the target sugar chain or glycopeptide.

After those tasks, the analysis operator issues a command to continue the quantitative determination process. Then, the peak area calculator 35 detects a peak on each of the mass chromatograms within their respective allowable ranges of the detection time and calculates the peak area. In the case of a normal quantitative analysis which is not aimed at multivalent ions (i.e. in which only a monovalent ion is considered), the quantitative value of the target compound is simply calculated based on the value of the peak area. On the other hand, in the case of a quantitative analysis in which multivalent ions are considered, the data processing is performed as follows.

The peak area totalizer 311 in the multivalent ion quantity calculator 310 reads the multivalent ion information file, which contains the association information, from the multivalent ion information file storage section 304. Based on the association information, the peak area totalizer 311 recognizes a plurality of MRM transitions associated with the same sugar chain or glycopeptide. For each sugar chain or glycopeptide, the peak area totalizer 311 adds up the peak areas calculated on the mass chromatograms for the plurality of MRM transitions which originate from the sugar chain or glycopeptide concerned, to obtain a total value of the peak areas.

In the example of FIG. 4, based on the association information, it is found that the mass chromatograms for the two MRM transitions with ionic numbers of three and four originate from the same sugar chain. Accordingly, the total value of the peak areas is calculated by adding up the peak areas respectively determined on the two mass chromatograms. The same also applies in the example of FIG. 5.

In this manner, the peak area totalizer 311 obtains the peak-area total value for each of all sugar chains set by the analysis operator before the execution of the measurement. Provided that there is no serious omission in the ionic valencies set by the analysis operator, the peak-area total value should correspond to the relative content of the sugar chain or glycopeptide concerned. Accordingly, the quantitative value calculator 312 calculates the grand total of the peak areas by adding up the peak-area total values obtained for all sugar chains or glycopeptides, and calculates the ratio (in percentage) of the peak-area total value of each sugar chain or glycopeptide to the grand total of the peak areas, as the quantitative value of the sugar chain or glycopeptide concerned.

If the sugar chains or glycopeptides which were set by the analysis operator before the execution of the measurement include all sugar chains or glycopeptides contained in the sample, the ratio of the peak-area total value calculated in the previously described manner indicates the abundance ratio of the corresponding sugar chain or glycopeptide in the sample. The quantitative output information creator 313 compiles the abundance ratios calculated for the sugar chains or glycopeptides into a graphical or tabular form and displays the graph or table on the screen of the display unit 5 as the result of the quantitative analysis.

Figure 6:
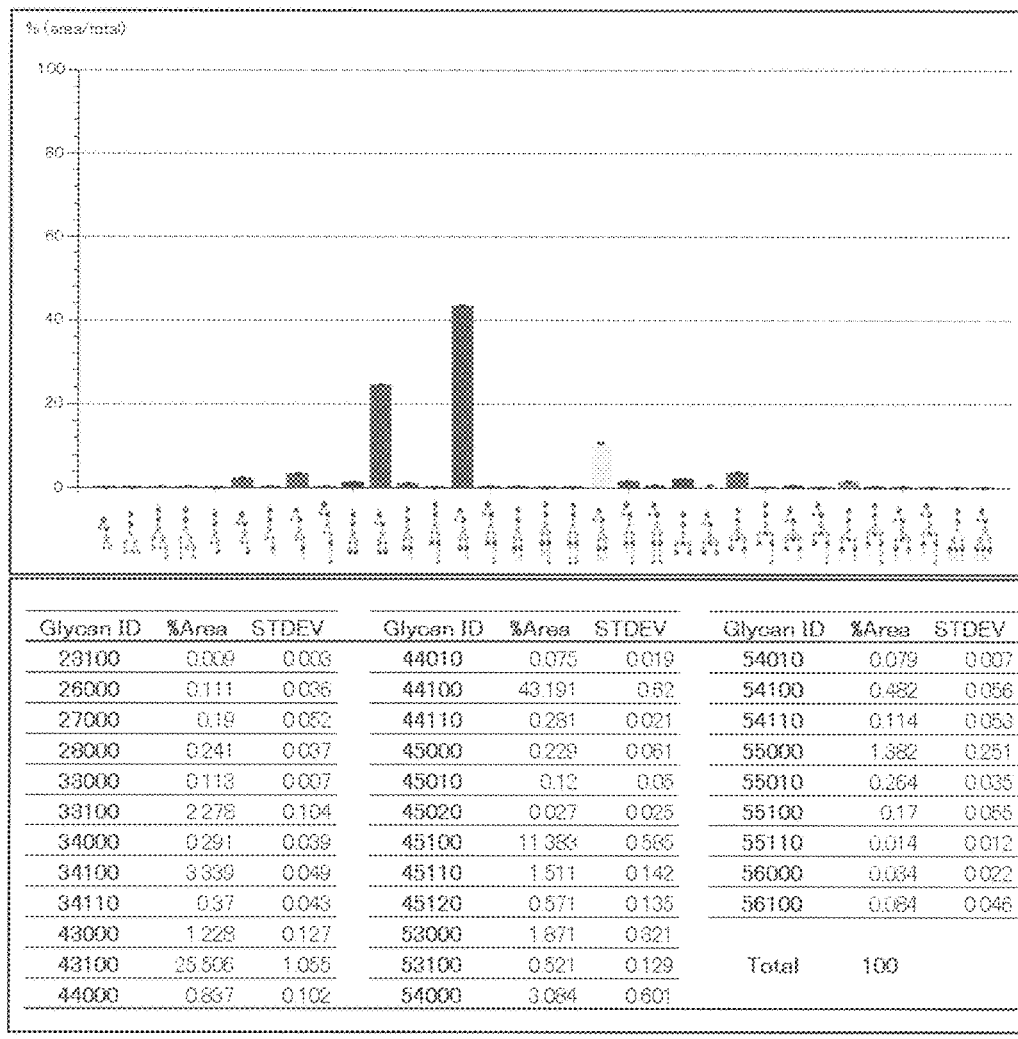
FIG. 6 is one example of the graph and table showing abundance ratios of sugar chains which are the results of quantitative analyses in quantitative analyzer according to the present embodiment.

FIG. 6 shows one example of the result of the quantitative analysis displayed on the screen of the display unit 5. In this example, the table in the lower area shows abundance ratios and standard deviations for 33 kinds of sugar chains, while the bar chart in the upper area shows the abundance ratios for the 33 sugar-chain structures. By viewing this display, the analysis operator can intuitively grasp the abundance ratios of the sugar chains or glycopeptides contained in the sample. It is naturally possible to display only the abundance ratios of specific sugar chains or glycopeptides selected by the analysis operator, instead of exhaustively displaying the abundance ratios of all sugar chains or glycopeptides. It is also possible to selectively display sugar chains or glycopeptides whose abundance ratios are higher or lower than a predetermined value.

In the previously described embodiment, the present invention is applied to the quantitative determination of sugar chains or glycopeptides. The present invention can be generally applied to the quantitative determination of any kind of high-molecular compounds from which a common product ion will be generated regardless of their chemical structures. In the quantitative analyzer according to the previous embodiment, a mass spectrometric analysis is performed after the components in a sample are temporally separated by the liquid chromatograph. If the number of components in the sample is small, and if the sample does not contain any other component which has the same mass and a different structure, the sample may be directly introduced into the mass spectrometer for mass spectrometry, without being passed through the liquid chromatograph.

The previous embodiment is a mere example of the present invention, and any change, modification, addition or the like appropriately made within the spirit of the present invention will naturally fall within the scope of claims of the present application.

REFERENCE SIGNS LIST

2 . . . Measurement Unit
20 . . . Liquid Chromatograph
21 . . . Tandem Quadrupole Mass Spectrometer
3 . . . Controlling-Processing Unit
31 . . . Analysis Controller
32 . . . Data Collector
33 . . . Data Storage Section
34 . . . Chromatogram Creator
35 . . . Peak Area Calculator
300 . . . Measurement Target Setter
301 . . . Precursor m/z Calculator
302 . . . Measurement Condition Setter
303 . . . Multivalent Ion Information File Creator
304 . . . Multivalent Ion Information File Storage Section
305 . . . Method File Creator
306 . . . Method File Storage Section
310 . . . Multivalent Ion Quantity Calculator
311 . . . Peak Area Totalizer
312 . . . Quantitative Value Calculator
313 . . . Quantitative Output Information Creator
4 . . . Input Unit
5 . . . Display Unit

The invention claimed is:

1. A method for a quantitative analysis for determining a quantity of a high-molecular compound in a sample using a mass spectrometer capable of an MS/MS analysis, the method comprising:

a) a peak information acquisition step, in which a total value of areas of peaks appearing on a plurality of mass chromatograms respectively acquired by a plurality of MRM measurements is calculated for a high-molecular compound which is an analysis target or is assumed to be an analysis target, the plurality of MRM measurements performed for a plurality of precursor ions which originate from the high-molecular compound yet differ from each other in ionic valency and one product ion which is common to the precursor ions; and b) a quantitative determination step, in which a quantity calculation of the high-molecular compound which is the analysis target or is assumed to be the analysis target is performed using the total value obtained in the peak information acquisition step.

2. The method for a quantitative analysis of a high-molecular compound according to claim 1, wherein:
the high-molecular compound is a sugar chain or glycopeptide.

3. The method for a quantitative analysis of a high-molecular compound according to claim 2, wherein:
the sample is a mixture of sugar chains or glycopeptides;
the total values for a plurality of sugar chains or glycopeptides contained in the sample are respectively obtained in the peak information acquisition step;
an abundance ratio of any specific sugar chain or glycopeptide is determined in the quantitative determination step, based on the total value obtained for the specific sugar chain or glycopeptide in the peak information acquisition step and a sum of the total values obtained for the plurality of sugar chains or glycopeptides contained in the sample; and
the method further comprises a quantitative determination result presentation step in which the abundance ratio of the specific sugar chain or glycopeptide obtained in the quantitative determination step is presented in a graphical or tabular form on a screen of a display section.

4. The method for a quantitative analysis of a high-molecular compound according to claim 1, wherein:
a measurement of the high-molecular compound in the sample is performed using a liquid chromatograph mass spectrometer including a liquid chromatograph connected in a previous stage of the mass spectrometer.

5. A data-processing device for determining a quantity of a high-molecular compound in a sample based on data acquired by using a mass spectrometer capable of an MS/MS analysis, the data-processing device comprising:
a) a peak information acquirer for calculating a total value of areas of peaks appearing on a plurality of mass chromatograms respectively acquired by a plurality of MRM measurements for a high-molecular compound which is an analysis target or is assumed to be an analysis target, the plurality of MRM measurements performed for a plurality of precursor ions which originate from the high-molecular compound yet differ from each other in ionic valency and one precursor ion which is common to the precursor ions; and b) a quantitative determination processor for performing a quantity calculation of the high-molecular compound which is the analysis target or is assumed to be the analysis target, using the total value obtained by the peak information acquirer.

6. The data-processing device according to claim 5, wherein:
the high-molecular compound is a sugar chain or glycopeptide.

7. The data-processing device according to claim 6, wherein:
the sample is a mixture of sugar chains or glycopeptides;
the peak information acquirer obtains the total values respectively for a plurality of sugar chains or glycopeptides contained in the sample;
the quantitative determination processor determines an abundance ratio of any specific sugar chain or glycopeptide, based on the total value obtained for the specific sugar chain or glycopeptide by the peak information acquirer and a sum of the total values obtained for the plurality of sugar chains or glycopeptides contained in the sample; and
the data-processing device further comprises a quantitative determination result presenter for presenting the abundance ratio of the specific sugar chain or glycopeptide obtained by the quantitative determination processor, in a graphical or tabular form on a screen of a display section.

8. The method for a quantitative analysis of a high-molecular compound according to claim 2, wherein:
a measurement of the high-molecular compound in the sample is performed using a liquid chromatograph mass spectrometer including a liquid chromatograph connected in a previous stage of the mass spectrometer.

9. The method for a quantitative analysis of a high-molecular compound according to claim 3, wherein:
a measurement of the high-molecular compound in the sample is performed using a liquid chromatograph mass spectrometer including a liquid chromatograph connected in a previous stage of the mass spectrometer.

* * * * *